(12) United States Patent
Takada et al.

(10) Patent No.: US 9,234,133 B2
(45) Date of Patent: Jan. 12, 2016

(54) ETCHING GAS

(71) Applicant: Central Glass Company, Limited, Ube-shi, Yamaguchi (JP)

(72) Inventors: Naoto Takada, Saitama (JP); Isamu Mori, Tokyo (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/455,128

(22) Filed: Aug. 8, 2014

(65) Prior Publication Data

US 2014/0349488 A1    Nov. 27, 2014

Related U.S. Application Data

(62) Division of application No. 13/513,038, filed as application No. PCT/JP2010/070656 on Nov. 19, 2010, now abandoned.

(30) Foreign Application Priority Data

Dec. 1, 2009  (JP) ................................. 2009-273031

(51) Int. Cl.
*H01L 21/302* (2006.01)
*C09K 13/00* (2006.01)
(Continued)

(52) U.S. Cl.
CPC .................. *C09K 13/00* (2013.01); *C07C 53/48* (2013.01); *C23F 1/12* (2013.01); *H01L 21/3065* (2013.01); *H01L 21/31116* (2013.01)

(58) Field of Classification Search
CPC ...................... H01L 21/3065; H01L 21/31105; H01L 21/31116; H01L 21/30655; C09K 13/00; C09K 13/06; C09K 13/08
USPC ......... 438/706, 710, 712, 714, 717, 725, 736; 252/79, 79.3, 79.4
See application file for complete search history.

(56) References Cited

U.S. PATENT DOCUMENTS

| 4,357,282 A | 11/1982 | Anderson et al. |
| 5,710,317 A | 1/1998 | Oharu et al. |

(Continued)

FOREIGN PATENT DOCUMENTS

| CN | 1902745 A | 1/2007 |
| EP | 1 760 769 A1 | 3/2007 |

(Continued)

OTHER PUBLICATIONS

PCT/ISA/237 Form (Three (3) pages).
(Continued)

*Primary Examiner* — Lan Vinh
(74) *Attorney, Agent, or Firm* — Crowell & Moring LLP

(57) ABSTRACT

Disclosed is an etching gas provided containing $CHF_2COF$. The etching gas may contain, as an additive, at least one kind of gas selected from $O_2$, $O_3$, CO, $CO_2$, $F_2$, $NF_3$, $Cl_2$, $Br_2$, $I_2$, $XF_n$ (In this formula, X represents Cl, I or Br. n represents an integer satisfying $1 \leq n \leq 7$.), $CH_4$, $CH_3F$, $CH_2F_2$, $CHF_3$, $N_2$, He, Ar, Ne, Kr and the like, from $CH_4$, $C_2H_2$, $C_2H_4$, $C_2H_6$, $C_3H_4$, $C_3H_6$, $C_3H_8$, HI, HBr, HCl, CO, NO, $NH_3$, $H_2$ and the like, or from $CH_4$, $CH_3F$, $CH_2F_2$ and $CHF_3$. This etching gas is not only excellent in etching performances such as the selection ratio to a resist and the patterning profile but also easily available and does not substantially by-produce $CF_4$ that places a burden on the environment.

13 Claims, 1 Drawing Sheet

(51) Int. Cl.
*H01L 21/3065* (2006.01)
*C07C 53/48* (2006.01)
*H01L 21/311* (2006.01)
*C23F 1/12* (2006.01)

(56) References Cited

U.S. PATENT DOCUMENTS

| | | | |
|---|---|---|---|
| 5,905,169 | A | 5/1999 | Jacobson |
| 5,994,599 | A | 11/1999 | Petrov |
| 6,242,359 | B1 * | 6/2001 | Misra ............................ 438/710 |
| 6,787,053 | B2 | 9/2004 | Sekiya et al. |
| 6,794,313 | B1 * | 9/2004 | Chang ........................... 438/770 |
| 6,962,853 | B2 | 11/2005 | Segawa et al. |
| 2001/0020707 | A1 | 9/2001 | Segawa et al. |
| 2003/0001134 | A1 | 1/2003 | Sekiya et al. |
| 2004/0069747 | A1 * | 4/2004 | Patel et al. ...................... 216/59 |
| 2004/0129671 | A1 * | 7/2004 | Ji et al. ............................ 216/58 |
| 2005/0101126 | A1 | 5/2005 | Wagganer et al. |
| 2007/0224829 | A1 * | 9/2007 | Ji et al. .......................... 438/710 |
| 2012/0234351 | A1 | 9/2012 | Takada et al. |

FOREIGN PATENT DOCUMENTS

| | | |
|---|---|---|
| JP | 8-92162 A | 4/1996 |
| JP | 8-191062 A | 7/1996 |
| JP | 2000-63826 A | 2/2000 |
| JP | 2000-265275 A | 9/2000 |
| JP | 2001-203349 A | 7/2001 |
| JP | 2002-158181 A | 5/2002 |
| JP | 2007-511096 A | 4/2007 |
| WO | WO 96/29298 A1 | 9/1996 |

OTHER PUBLICATIONS

International Search Report including English language translation dated Jan. 25, 2011 (Five (5) pages).
European Search Report dated Apr. 12, 2013 (seven (7) pages).
Isao Tari et al., "Synthesis of Halogenated Esters of Fluorinated Carboxylic Acids by the Regio- and Stereospecific Addition of Acyl Hypochlorites to Olefins", J. Org. Chem., vol. 45, No. 7, 1980, pp. 1214-1217, XP-001055041.
Taiwanese Office Action dated Aug. 28, 2013 (five (5) pages).
Chinese Office Action with Japanese translation dated Oct. 29, 2013 (Sixteen (16) pages).

* cited by examiner

ETCHING GAS

CROSS REFERENCE TO RELATED APPLICATIONS

This application is a divisional of U.S. application Ser. No. 13/513,038, filed May 31, 2012, which is a national stage of PCT/JP2010/070656 filed on Nov. 19, 2010, which claims priority from Japanese Application No. 2009-273031 filed on Dec. 1, 2009, the disclosures of which are expressly incorporated by reference herein.

TECHNICAL FIELD

The present invention relates to an etching gas used for producing thin film devices represented by IC, LSI, TFT and the like, and particularly to an etching gas that accomplishes both environmental performances and micro-patterning performances.

BACKGROUND OF THE INVENTION

In processes for producing semiconductor thin film devices, optical devices, super steel materials and the like, there have been produced various thin films, thick films and the like by means of CVD method, sputtering method, sol-gel method, vapor deposition method and the like. Moreover, in order to form a circuit pattern, gas etching for partially removing a thin film material has been conducted on semiconductors or in fabrication of semiconductors for IC, LSI, TFT and the like.

Hitherto, perfluorocarbons (PFCs) such as $CF_4$, $C_2F_6$, $C_3F_8$ and the like have been used as an etching gas in etching for forming circuits, in fabrication of thin film devices. However, these gases exist in the environment stably for a long period of time and therefore regarded as having high global warming potentials, so that their adverse influence on the environment has come to an issue.

For example, their GWPs known from the IPCC *Fourth Assessment Report* are as follows (on a 100 year scale):

$CF_4$: 7390

$C_2F_6$: 12200

$C_3F_8$: 8830

An etching gas partially having the structure of $CF_3$ group e.g. $C_2F_6$, $C_3F_8$ and the like generates active species exemplified by $CF_3$ radicals, ions and the like in a deposition room (a chamber) thereby exhibiting the etching effect; however, $CF_3$ active species are brought into contact with fluorine radicals or with fluorine active species of ions to be recombined thereto, thereby forming $CF_4$ as a by-product.

Guidelines on the destruction of PFCs issued by Office of Fluorocarbons Control Policy, Global Environmental Issues Division of the Global Environment Bureau of the Ministry of the Environment (issued in March 2009) states that $CF_4$ is the most undecomposable PFC in the environment and therefore it may not be sufficiently destructed under the destructing conditions similar to those for other fluorocarbons.

As a fluorine-containing etching gas having low global warming potentials and substitutable for PFC, there have been proposed $COF_2$, $CHF_2OF$ (Patent Publication 1), $CF_3COF$ (Patent Publications 2 and 3) and the like. These publications state it is possible to reduce by-production of $CF_4$, for example, by optimizing an etching condition for $CF_3COF$.

REFERENCES ABOUT PRIOR ART

Patent Publication

Patent Publication 1: Japanese Patent Application Publication No. 2000-63826

Patent Publication 2: Japanese Patent Application Publication No. 2000-265275

Patent Publication 3: Japanese Patent Application Publication No. 2002-158181

SUMMARY OF THE INVENTION

As mentioned above, Patent Publications 1 and 2 state that by-production of $CF_4$ can be reduced by optimizing an etching condition for $CF_3COF$. However, it is considered difficult to fundamentally avoid a recombination of the $CF_3$ active species and the fluorine active species so long as the etching gas partially having the structure of $CF_3$ group is used. In view of the above, the optimized etching condition is found not to be optimized in respect of the micro-patterning speed and the patterning accuracy, which means that the aimed patterning accuracy and the like are restricted by the rate of $CF_4$ by-production. In fact, there are not a few cases difficult to constantly reduce by-production of $CF_4$ under a condition satisfying required performances such as the etching rate, the anisotropy, the aspect ratio, the resist ratio and the like.

In order to obtain a good anisotropy in etching that requires micro-patterning performances, a compound having a ratio of fluorine number to carbon number (F/C) close to 1 in a is demanded. For example, in the case of perfluorocarbons, F/C of $CF_4$ is 4, F/C of $C_2F_6$ is 3 and F/C of $C_3F_8$ is 2.7. As the carbon number gets increased, F/C thus approaches 1 or the above-mentioned requirement, but the boiling point also gets increased so as to become difficult to handle as gas. Moreover, F/C of $CF_3COF$ is 2 and therefore it is not a satisfying value too.

In view of the above, an object of the present invention is to provide a novel etching gas which is not only excellent in etching performances but also easily available and does not substantially by-produce $CF_4$ that places a burden on the environment.

The present inventors had eagerly made studies on the above-mentioned object and thereby found that $CHF_2COF$ can accomplish both the environmental performances and the environmental safety, with which the present invention has come to completion. More specifically, the present invention is as follows.

Invention 1

An etching gas used for etching semiconductors, dielectric substances or thin films formed of metals, comprising $CHF_2COF$.

Invention 2

An etching gas of Invention 1, wherein the semiconductors or the dielectric substances are a silicon-containing substance.

Invention 3

An etching gas of Invention 1, wherein the etching gas contains at least one kind of gas selected from $O_2$, $O_3$, CO, $CO_2$, $F_2$, $NF_3$, $Cl_2$, $Br_2$, $I_2$, $XF_n$ (In this formula, X represents Cl, I or Br. n represents an integer satisfying 1≤n≤7.), $CH_4$, $CH_3F$, $CH_2F_2$, $CHF_3$, $N_2$, He, Ar, Ne and Kr, as an additive.

Invention 4

An etching gas of Invention 1, wherein the etching gas contains at least one kind of gas selected from $CH_4$, $C_2H_2$, $C_2H_4$, $C_2H_6$, $C_3H_4$, $C_3H_6$, $C_3H_8$, HI, HBr, HCl, CO, NO, $NH_3$, $H_2$, $N_2$, He, Ar, Ne and Kr, as an additive.

Invention 5

An etching gas of Invention 1, wherein the etching gas contains at least one kind of gas selected from $CH_4$, $CH_3F$, $CH_2F_2$, $CHF_3$, as an additive.

Invention 6

A method for etching semiconductor films, dielectric films or metal films, comprising the step of: using an etching gas of Invention 1.

Invention 7

A method for etching, of Invention 6, further comprising the step of: thereafter ashing by $F_2$ or $O_2$.

DETAILED DESCRIPTION

Figure 1A:
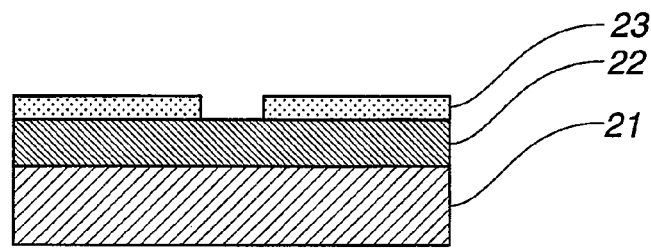
FIG. 1A A schematic cross section of a sample for etching used in Examples and Comparative Examples.

The etching gas according to the present invention is not only characterized by placing a slight burden on the environment by virtue of its containing $CHF_2COF$ but also exhibits good etching performances in semiconductor film-forming process, i.e., a performance of high etching rates, a performance of not bringing corrosion to the apparatus and the like. Hence the etching gas is useful for micro-patterning conducted on thin films by etching in semiconductor film-forming process.

The present invention will be hereinafter discussed in detail.

$CHF_2COF$ can be readily and rationally synthesized by catalytic cracking of 1-alkoxy-1,1,2,2-tetrafluoroethane represented by $CHF_2CF_2OR$ (where R is an alkyl group including Me, Et, n-Pr, iso-Pr, n-Bu, sec-Bu, iso-Bu, tert-Bu and the like) and used as a cleaning agent, a foaming agent or the like such as HFE-254pc ($CHF_2CF_2OMe$), HFE-374pc-f ($CHF_2CF_2OEt$) and the like. Moreover, HFE-254pc and HFE-374pc-f can be synthesized by adding methanol or ethanol to an industrially mass-produced tetrafluoroethylene so as to be greatly available compounds.

$CHF_2COF$ has a boiling point of 0° C. and therefore serves as a highly convenient etching gas that can be handled as either liquid or gas. Additionally, $CHF_2COF$ is reacted with water to be decomposed into difluoroacetic acid ($CHF_2COOH$) and hydrogen fluoride (HF), so that usually its hazard can be eliminated by using a water scrubber. It is also preferable to use an alkaline water scrubber. Even in the event of passing the hazard-eliminating step so as to be emitted into the air, $CHF_2COF$ is reacted with rain and steam in the air thereby being readily decomposed. Thus its environmental impact is extremely minimal.

As a point where $CHF_2COF$ of the present invention is significantly different from the existing $CF_3COF$ in property, it is possible to cite an easiness to establish a ketene structure. $CHF_2COF$ is known to be able to take on a ketene structure represented by $CF_2=C=O$ as shown in the following equation. In the case of $CF_3COF$, a reaction for taking on the ketene structure is an endothermic reaction calculated at 165.9 kcal. In order to develop this reaction a further activation energy is required in addition to the above free energy, so that the likelihood of this reaction can be said to be actually remarkably little.

$CHF_2COF \rightarrow CF_2=C=O+HF+48.9$ kcal/mol

$CF_3COF \rightarrow CF_2=C=O+F_2+165.9$ kcal/mol

The heat of reaction is a value calculated by B3LYP/6-311G+**.

As will be discussed in Examples, in the cases of using $CHF_2COF$ as the etching gas, $CF_4$ was not detected at all even under variously modified conditions. It can be supposed from this fact that etching was developed through a vastly different mechanism from $CF_3COF$.

Furthermore, in the case of using $CF_3COF$, once generated $CF_3$ active species are brought into contact with fluorine active species with a certain probability to cause recombination thereby by-producing $CF_4$ (in an etching process employing plasma, for example). On the contrary, in the case of using $CHF_2COF$, by-production remains at $CHF_3$ which is relatively reasonably decomposable even if $CHF_2$ active species and fluorine active species are brought into contact with each other. Stochastically there is the possibility that $CHF_3$ is so decomposed as to form $CF_3$ active species and it is bonded to the fluorine active species again thereby to by-produce $CF_4$; however, it is easily supposed that such a probability is extremely small as compared to etching gases partially having the structure of $CF_3$ group ($CF_3COF$, etc.). For the above reasons $CHF_2COF$ is considered not to substantially by-produce $CF_4$. As a matter of fact, by-production of $CF_4$ was not recognized in any of the Examples.

The etching gas containing $CHF_2COF$ according to the present invention can be particularly preferably used for etching of: semiconductors when manufacturing semiconductor devices; dielectric substances; or thin films formed of metals.

As substances able to be etched by the etching gas containing $CHF_2COF$ according to the present invention, it is possible to cite B, P, W, Si, Ti, V, Nb, Ta, Se, Te, Mo, Re, Os, Ru, Ir, Sb, Ge, Au, Ag, As, Cr, Hf, Zr, Ni, Co and their compounds deposited on semiconductor substrates such as silicon wafers, GaAs wafers and the like, metal substrates such as W, Ta, Mo and the like, insulating or dielectric substrates such as $SiO_2$, $Al_2O_3$, $Ta_2O_3$ and the like, glasses such as soda-lime glasses, borosilicate glasses and the like, or substrates formed of single crystals or polycrystals of other compounds or the like. Among them, this etching gas is particularly effective at etching oxides, nitrides, carbides, or composites of them. It is particularly preferable to use W, $WSi_x$, Ti, TiN, $Ta_2O_5$, Mo, Re, Ge, $Si_3N_4$, Si, $SiO_2$ or the like, more preferably silicon-containing substances such as $WSi_x$, $Si_3N_4$, Si, $SiO_2$ and the like, and much more preferably Si or $SiO_2$. The above-mentioned substances may be any of single crystal, polycrystal and amorphous form.

The etching gas of the present invention can be used for etching exemplified by RIE (reactive-ion etching), ECR (electron cyclotron resonance) plasma etching, microwave etching and the like, but not limited to these. Additionally, these kinds of etching processes are a common knowledge among the skilled in the art and can be referred to from publications as needed. The reaction conditions are not required particularly. When $CHF_2COF$ is used, fluorine radicals reach recessed portions of channels and then $CFy$ ions (where y represents an integer of from 1 to 3) enter there, with which etching develops in a longitudinal direction. Side walls are protected by deposition of a fluorocarbon polymer, thereby preventing an isotropic etching due to fluorine radicals and allowing an anisotropic etching. Moreover, since $CHF_2COF$ contains oxygen (O), there is an advantage that the anisotropic etching can be developed while efficiently removing fluorocarbon films deposited on the side walls.

As a reason for the specifically good micro-patterning of $CHF_2COF$, it is possible to cite not only the fact that a ratio represented by F/C is 1.5 in the case of $CHF_2COF$ while it is 2 in the case of $CF_3COF$ but also the effect of the above-mentioned ketene which is polymerized to protect the side walls. It is also possible to remove organic substances including polymers, in such a manner as to carry out heating by using an oxidizing gas such as $F_2$, $O_2$ and the like or to carry out plasma ashing after conducting etching by using the etching gas of the present invention, An etching method of the present invention is practicable under various dry etching conditions and allows the addition of various additives depending on the property, productivity, micro-patterning accuracy and the like of the target film. Inert gases exemplified by $N_2$, He, Ar, Ne, Kr and the like are usable as a diluent, and more particularly, Ar is effective at stabilizing plasma and therefore provides an enhanced etching rate by a synergistic effect with $CHF_2COF$. Though the amount of the added inert gases depends on the configuration and performances of the apparatus such as the output, the amount of discharged gas and the like or on the properties of the target film, it is preferably 1/10 to 30 times the amount of flow of $CHF_2COF$.

With the addition of the oxidizing gas to $CHF_2COF$, it becomes possible to increase the etching rate and to enhance the productivity. Concrete examples thereof are $O_2$, $O_3$, $CO_2$, $F_2$, $NF_3$, $Cl_2$, $Br_2$, $I_2$, $XF_n$ (In this formula, X represents Cl, I or Br. n represents an integer satisfying $1 \leq n \leq 7$. Concrete examples are ClF, $ClF_3$, BrF, $BrF_3$, $IF_5$ and $IF_7$.). Though the amount of the added oxidizing gas depends on the configuration and performances of the apparatus such as the output and the like or on the properties of the target film, it is usually 1/20 to 30 times the amount of flow of $CHF_2COF$, more preferably 1/10 to 10 times the amount of flow of $CHF_2COF$. The addition exceeding 30 times impairs the excellent anisotropic etching performance of $CHF_2COF$ and therefore not preferable. In the case of less than 1/20, the effect of the addition of the oxidizing gas cannot be sufficiently exhibited and therefore not preferable. In particular, the addition of oxygen allows selectively accelerating the etching rate on metals, and more specifically, greatly improves the selection ratio of the etching rate on metals thereby allowing a selective etching on metals. It is a matter of course that the addition of inert gases such as $N_2$, He, Ar, Ne, Kr and the like in addition to the oxidizing gas is acceptable as desired.

If reduction of the amount of fluorine radicals that accelerates the isotropic etching is required, the addition of a reducing gas exemplified by $CH_4$, $C_2H_2$, $C_2H_4$, $C_2H_6$, $C_3H_4$, $C_3H_6$, $C_3H_8$, HI, HBr, HCl, CO, NO, $NH_3$ and $H_2$ provides a good effect. The amount of the addition is preferably not larger than 10 times. When the addition exceeds the above, fluorine radicals that work on etching is significantly reduced thereby decreasing the productivity. Particularly, the addition of $H_2$ or $C_2H_2$ decreases the etching rate on Si while the etching rate on $SiO_2$ is not changed, so that the selectivity is enhanced. Thus it becomes possible to etch $SiO_2$ selectively against a foundation silicon.

Furthermore, gases having a carbon number of 1 such as $CH_4$, $CH_3F$, $CH_2F_2$ and $CHF_3$ are effective in a fine-tuning of the ratio of fluorine to carbon in the etching gas. The amount of the addition thereof also is preferably not larger than 10 times the amount of $CHF_2COF$. When the addition exceeds the above, the excellent etching performances of $CHF_2COF$ get impaired. CO traps HF (which has been by-produced, for example when ketene is generated) in the form of HCOF and works as an etching agent in itself, so as to be efficiently used. The amount of CO to be added is from 10:1 to 1:5, preferably from 5:1 to 1:1 in a mole ratio represented by $CHF_2COF:CO$.

The pressure in the case of using the etching gas of the present invention is preferably not higher than 660 Pa (5 Torr) in order to perform anisotropic etching; however, pressures of not higher than 0.13 Pa (0.001 Torr) reduce the etching rate and therefore not preferable. The flow rate of gas to be used depends on the volume of a reactor of the etching apparatus and on the size of the wafer, but it is preferable to carry out etching at a flow rate of between 10 to 10000 SCCM. Moreover, the temperature for etching is preferably not greater than 400° C. High temperatures exceeding 400° C. are not preferable since etching tends to develop isotropically so that a desired patterning accuracy cannot be obtained and since a resist is excessively etched.

EXAMPLES

The present invention will be more readily understood with reference to the following Examples.

Examples 1 to 3 and Comparative Examples 1 and 2

There are shown examples where etching was conducted on an interlaminar insulating film ($SiO_2$) by using an etching gas of the present invention for contact hole-fabrication.

As a sample, a $SiO_2$ interlaminar insulating film 22 was formed on a single crystal silicon wafer 21. The sample was put to use upon forming on the $SiO_2$ film a resist mask 23 having apertures to serve as an etching mask. A sample before etching is shown in FIG. 1A.

Figure 2:
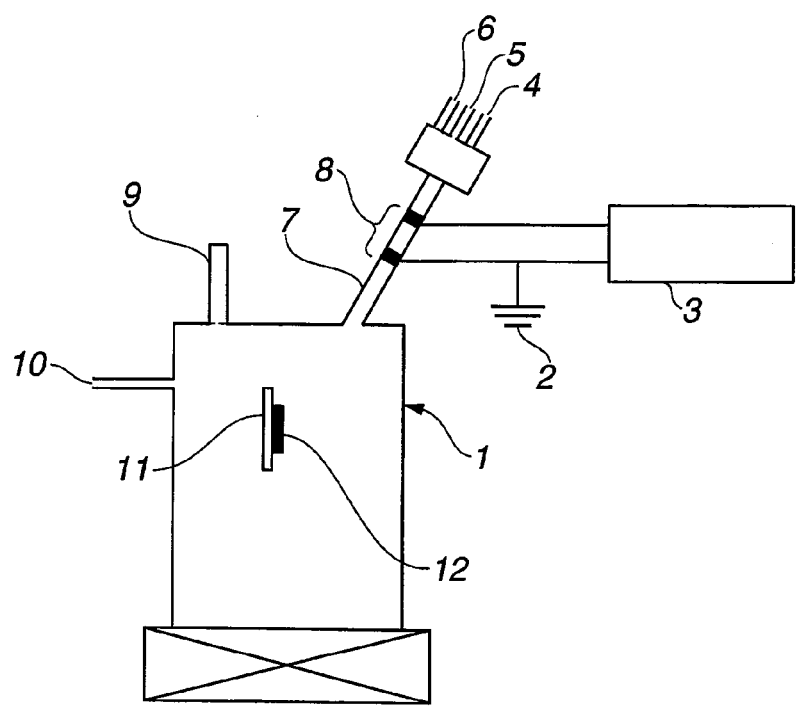
FIG. 2 A schematic cross section of a remote plasma apparatus used in Examples and Comparative Examples.

A schematic cross section of an apparatus used in the experiment is shown in FIG. 2. By using a high-frequency source 3 (13.56 MHz, 50 W), etching gases (difluoroacetyl fluoride ($CHF_2COF$), oxygen ($O_2$), argon (Ar)) having been supplied from a gas inlet at flow rates shown in Table 1 were excited in a sapphire tube 7 attached to the top of a reaction chamber 1 thereby generating active species. The active species were supplied into the chamber by the flow of gas, upon which etching was conducted on a sample 12 fixed by a sample holder 11. Among the gas specimens, $CHF_2COF$, $CF_3COF$ and $CF_4$ were introduced from a first gas inlet while $O_2$ was introduced from a second gas inlet, through a mass flow controller (though not shown).

Figure 1B:
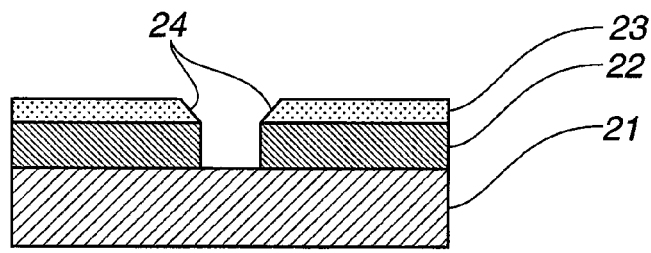
FIG. 1B A schematic cross section of a sample after etching (showing a case of having facets).

The temperature of the substrate (or the sample holder 11) was set at 25° C., the pressure was set at 2.67 Pa (0.02 Torr), and the RF power density was set at 2.2 W/cm². A discharged gas was diluted with nitrogen supplied at 5 L/min on a discharge side of a mechanical booster pump, and then the concentration of $CF_4$ was quantified by calibration curve method with the use of FT-IR. Results of the above are shown in Table 1. Incidentally, "ND" shown in the Table refers to less than the floor limit for detection (0.05 volume %). The etching rate (Å/min) was determined in such a manner as to divide film thicknesses obtained before and after etching by an etching time. The film thicknesses were measured by an optical interferotype film-thickness meter. A sample after etching (in the case of having facets) is shown in FIG. 1B.

TABLE 1

| | Gas 1 | Flow Rate of Gas 1 SCCM | Gas 2 | Flow Rate of Gas 2 SCCM | Etching Rate Å/min | Selection Ratio to Resist | Aspect Ratio | Patterning Profile | $CH_4$ Concentration in Discharged Gas |
|---|---|---|---|---|---|---|---|---|---|
| Example 1 | $CHF_2COF$ | 50 | None | — | 4085 | 6 | 6 or more | No facet, Good side wall | Less than floor limit for detection |
| Example 2 | $CHF_2COF$ | 10 | Ar | 200 | 4121 | 6 | 6 or more | No facet, Good side wall | Less than floor limit for detection |
| Example 3 | $CHF_2COF$ | 50 | $O_2$ | 10 | 15598 | 7 | 6 or more | No facet, Good Side wall | Less than floor limit for detection |
| Comparative Example 1 | $CF_3COF$ | 50 | None | — | 3218 | 5 | 6 or more | Partially having facets and gouges in side wall | 0.11% |
| Comparative Example 2 | $CF_4$ | 50 | None | — | 608 | 4 | 5 | Partially having facets and gouges in side wall | 0.18% |

$CHF_2COF$: Difluoroacetyl fluoride
$CF_3COF$: Trifluoroacetyl fluoride
$O_2$: Oxygen
Ar: Argon
$CF_4$: Carbon tetrafluoride

EXPLANATION OF REFERENCE NUMERALS

1 Chamber
2 Earth
3 High-frequency source
4 First gas inlet
5 Second gas inlet
6 Third gas inlet
7 Sapphire tube
8 Induction coil
9 Electronic pressure meter
10 Discharged-gas line
11 Sample holder
12 Sample
21 Silicon wafer
22 $SiO_2$ interlaminar insulating film
23 Resist mask
24 Facets

The invention claimed is:

1. A method, comprising etching a semiconductor, a dielectric substance, or a thin film formed of a metal with an etching gas comprising $CHF_2COF$.

2. The method of claim 1, wherein the semiconductor or the dielectric substance is a silicon-containing substance.

3. The method of claim 1, further comprising ashing the semiconductor, the dielectric substance, or the thin film formed of the metal with $F_2$ or $O_2$ after the etching.

4. The method of claim 1, wherein the etching is reactive-ion etching, etching by electron cyclotron resonance, plasma etching, or microwave etching.

5. The method of claim 1, wherein the etching gas further comprises at least one kind of gas selected from the group consisting of $CH_4$, $C_2H_2$, $C_2H_4$, $C_2H_6$, $C_3H_4$, $C_3H_6$, $C_3H_8$, HI, HBr, HCl, CO, NO, $NH_3$, $H_2$, $N_2$, He, Ar, Ne, and Kr as an additive.

6. The method of claim 5, wherein the etching gas comprises $CH_4$, $C_2H_2$, CAL, $C_2H_6$, $C_3H_4$, $C_3H_6$, $C_3H_8$, HI, HBr, HCl, CO, NO, $NH_3$, $H_2$, or combinations thereof in an amount of less than 10 times an amount of $CHF_2COF$.

7. The method of claim 1, wherein the etching gas further comprises at least one kind of gas selected from the group consisting of $CH_4$, $CH_3F$, $CH_2F_2$, and $CHF_3$ as an additive.

8. The method of claim 7, wherein the etching gas comprises $CH_4$, $CH_3F$, $CH_2F_2$, $CHF_3$, or combinations thereof in an amount less than 10 times an amount of $CHF_2COF$.

9. The method of claim 1, wherein the etching gas further comprises at least one kind of gas selected from the group consisting of $O_2$, $O_3$, CO, $CO_2$, $F_2$, $NF_3$, $Cl_2$, $Br_2$, $I_2$, $XF_n$, $CH_4$, $CH_3F$, $CH_2F_2$, $CHF_3$, $N_2$, He, Ar, Ne, and Kr as an additive, wherein X represents Cl, I or Br and n represents an integer $1 \leq n \leq 7$.

10. The method of claim 9, wherein the etching gas comprises $O_2$, $O_3$, $CO_2$, $F_2$, $NF_3$, $Cl_2$, $Br_2$, $I_2$, $XF_n$, or combinations thereof in an amount of 1/20 to 30 times an amount of $CHF_2COF$.

11. The method of claim 9, wherein the etching gas comprises $O_2$, $O_3$, $CO_2$, $F_2$, $NF_3$, $Cl_2$, $Br_2$, $I_2$, $XF_n$, or combinations thereof in an amount of 1/10 to 10 times an amount of $CHF_2COF$.

12. The method of claim 9, wherein the etching gas comprises CO in a mole ratio of $CHF_2COF$:CO of 10:1 to 1:5.

13. The method of claim 9, wherein the etching gas comprises CO in a mole ratio of $CHF_2COF$:CO of 5:1 to 1:1.

\* \* \* \* \*